(12) United States Patent
McBeth et al.

(10) Patent No.: US 12,370,220 B2
(45) Date of Patent: Jul. 29, 2025

(54) COMPOSITION OF MATTER AND METHODS FOR A FECAL-DERIVED STERILIZED PREBIOTIC AND POSTBIOTIC

(71) Applicant: THAENA INC., Vancouver, WA (US)

(72) Inventors: Andrea McBeth, Portland, OR (US); Piper Dobner, Milwaukie, OR (US)

(*) Notice: Subject to any disclaimer, the term of this patent is extended or adjusted under 35 U.S.C. 154(b) by 17 days.

(21) Appl. No.: 17/721,908

(22) Filed: Apr. 15, 2022

(65) Prior Publication Data

US 2023/0089315 A1 Mar. 23, 2023

Related U.S. Application Data

(63) Continuation-in-part of application No. PCT/US2020/056131, filed on Oct. 16, 2020.

(60) Provisional application No. 63/178,468, filed on Apr. 22, 2021, provisional application No. 62/923,174, filed on Oct. 18, 2019.

(51) Int. Cl.
| | |
|---|---|
| *A61K 35/24* | (2015.01) |
| *A61K 9/19* | (2006.01) |
| *A61K 31/19* | (2006.01) |
| *A61K 31/198* | (2006.01) |

(52) U.S. Cl.
CPC ............... *A61K 35/24* (2013.01); *A61K 9/19* (2013.01); *A61K 31/19* (2013.01); *A61K 31/198* (2013.01)

(58) Field of Classification Search
None
See application file for complete search history.

(56) References Cited

U.S. PATENT DOCUMENTS

| | | |
|---|---|---|
| 2008/0019952 A1 | 1/2008 | Kolossov et al. |
| 2011/0213567 A1 | 9/2011 | Haque et al. |
| 2012/0059599 A1 | 3/2012 | Cunningham et al. |
| 2013/0231264 A1 | 9/2013 | Reichman et al. |
| 2017/0298436 A1 | 10/2017 | Kaseniit et al. |

FOREIGN PATENT DOCUMENTS

| | | | | |
|---|---|---|---|---|
| KR | 2015-0103012 A | * | 10/2015 | |
| WO | WO-2018140931 A1 | * | 8/2018 | ............. A61K 35/74 |

OTHER PUBLICATIONS

KR2015-0103012A translated doc (Year: 2015).*
Tuttnauer, retrieved on Nov. 15, 2023 (https://tuttnauer.com/blog/autoclave) Nov. 2, 2015, 7 pages. (Year: 2015).*
AAFCO retrieved on Feb. 5, 2024 (https://www.aafco.org/wp-content/uploads/2023/01/Listing-of-communition-equipment-2018.pdf) (Year: 2018).*
Wikidoc, retrieved on Jul. 1, 2024 (https://www.wikidoc.org/index.php/Comminution) lasted edited on Sep. 4, 2012. (Year: 2012).*
Primec et. al. (Analysis of short-chain fatty acids in human feces: A scoping review, Analytical Biochemistry 526 (2017) 9-21). (Year: 2017).*
Tuttnauer, "Autoclave Sterilization Process Guide", retrieved on Nov. 15, 2023 (https://tuttnauer.com/blog/autoclave) Nov. 2, 2015, 7 pages. (Year: 2015).
Mateos et al., "Automated Platforms for Reaction Self-Optimazation in Flow", React. Chem. Eng., Apr. 26, 2019, vol. 4 p. 1536-1544, Abstract; p. 5, col. 2, para 1; p. 6, col. 1, para 2.
International Search Report from PCT/US2020/056131.

* cited by examiner

*Primary Examiner* — J. E. Angell
*Assistant Examiner* — Jacob A Boeckelman
(74) *Attorney, Agent, or Firm* — Caldwell Intellectual Property Law

(57) ABSTRACT

Methods and compositions relating to sterilized fecal microbiota and compositions derived from the same. A method of sterilizing a fecal composition to obtain a sterilized fecal composition is provided. Methods of further purifying the sterilized composition and optionally freezing or freeze-drying the compositions is also provided. Methods of using the compositions for treatment in beverages, foods, and in supplements are also provided.

8 Claims, 15 Drawing Sheets

300

| Biochemical class | Total weight, μg per 50 mg capsule (SD) |
|---|---|
| Bile acids | 508.7 (134.9) |
| Fatty acids | 274.2 (63.0) |
| Amino acids | 262.4 (46.5) |
| Sugars | 138.2 (64.3) |
| Amino acid related | 37.8 (6.19) |
| Dihydroceramides | 16.4 (6.11) |
| Triacylglycerols | 14.2 (3.28) |
| Indole derivatives | 13.4 (4.98) |
| Nucleobases related | 10.1 (4.01) |
| Carboxylic acids | 9.74 (2.30) |
| Glycerophospholipids | 7.56 (2.97) |
| Glycosylceramides | 6.00 (1.61) |
| Biogenic amines | 5.37 (1.18) |
| Cholesterol esters | 3.70 (1.15) |
| Diacylglycerols | 3.25 (0.54) |
| Vitamins and cofactors | 1.03 (0.28) |
| Ceramides | 1.03 (0.39) |
| Acylcarnitines | 0.62 (0.17) |
| Alkaloids | 0.15 (0.08) |
| Sphingolipids | 0.14 (0.04) |
| Cresols | 0.05 (0.02) |
| Hormones | 0.04 (0.02) |
| Amine oxides | 0.03 (0.02) |

*FIG. 3*

SCFA Changes with increase in pH using NaOH

| Metabolite - SCFA | FMT (µg/g) | FSP (µg/g / %FMT) | FSP-1 pH 6.0 (µg/g / %FMT / %FSP) | FSP-1 pH 7.2 (µg/g / %FMT / %FSP) | FSP-1 pH 8.0 (µg/g / %FMT / %FSP) |
|---|---|---|---|---|---|
| 2-Methylbutyric acid | 13.3 | 15.8 / 119% | 6.7 / 50% / 42% | 8.9 / 67% / 56% | 10.0 / 75% / 63% |
| Acetic acid | 577 | 584 / 101% | 257.8 / 45% / 44% | 339.6 / 59% / 58% | 437.4 / 75% / 76% |
| Butyric acid | 355 | 399 / 112% | 185.2 / 52% / 46% | 246.1 / 69% / 62% | 283.0 / 80% / 71% |
| Hexanoic acid | 1.89 | 2.01 / 106% | 1.3 / 67% / 63% | 1.4 / 72% / 68% | 1.6 / 83% / 79% |
| Iso-butyric acid | 18.2 | 20.1 / 111% | 7.2 / 39% / 36% | 11.8 / 65% / 59% | 13.9 / 76% / 69% |
| Iso-valeric acid | 19.2 | 18.2 / 95% | 9.6 / 50% / 53% | 12.7 / 66% / 70% | 13.9 / 72% / 76% |
| Propionic acid | 201 | 223 / 111% | 93.5 / 47% / 42% | 124.2 / 62% / 56% | 173.9 / 86% / 78% |
| Valeric acid | 30.2 | 38.3 / 127% | 20.2 / 67% / 53% | 22.4 / 74% / 59% | 25.2 / 84% / 66% |

| Biochemical class | Metabolite | Average pmol/mg (% total of class) | Average pmol/mg (% total) |
|---|---|---|---|
| Fatty acids | | | 24,717 (21.5%) |
| | Fatty acid 18:2 | 13,464 (54.4%) | |
| | Fatty acid 16:0 | 10,977 (44.0%) | |
| Amino acids | | | 45,326 (39.4%) |
| | Alanine | 8,004 (17.7%) | |
| | Leucine | 5,593 (12.3%) | |
| | Valine | 4,702 (10.4%) | |
| | Isoleucine | 4,475 (9.9%) | |
| | Lysine | 2,808 (6.2%) | |
| | Tyrosine | 2,695 (5.9%) | |
| Bile acids | | | 28,476 (24.7%) |
| | Chenodeoxycholic acid (CDCA) | 17,231 (60.5%) | |
| | Deoxycholic acid (DCA) | 10,965 (38.5%) | |
| Amino acids-related | | | 6,121 (5.3%) |
| | 5-aminovaleric acid | 2,019 (33.0%) | |
| | Citrulline | 1,076 (17.6%) | |
| | Methionine sulfoxide | 911 (14.9%) | |
| Indole derivatives | | | 3,071 (2.7%) |
| | Indole | 3,042 (99.1%) | |
| Sugars | | | 2,440 (2.1%) |
| | D-glucose | 2,440 (100%) | |
| Carboxylic acids | | | 1,847 (1.6%) |
| | L-lactic acid | 1,331 (72.1%) | |
| Nucleobase-related | | | 1,476 (1.3%) |
| | Xanthine | 846 (57.4%) | |
| | Hypoxanthine | 629 (42.6%) | |
| Biogenic amines | | | 1,202 (1.0%) |
| | Beta alanine | 531 (44.2%) | |
| | Gamma aminobutyric acid | 480 (39.9%) | |
| Vitamins & cofactors | | | 217 (0.2%) |
| | Choline | 217 (100%) | |
| Dihydroceramides | | | 46.69 (0.04%) |
| | D18:0/16:0 | 44.27 (90.5%) | |

*FIG. 7A*

| Chemical name (CAS) | Toxicity test | Oral dose mg/kg (animal model) | Quantified amount (mg/50 mg cap) |
|---|---|---|---|
| Imidazole (288-32-4) | LD$_{50}$ | 760 (guinea pig) 880 (mouse) 220 (rat) | 0.51%* |
| Spermidine (124-20-9) | LD$_{50}$ | >1,000 (mouse) | .00010 |
| 7 ketocholesterol (566-28-9) | | 750 (mouse) | 0.055%* |
| p cresol sulfate (91975-64-7) | N/A | N/A | 000061 |
| p cresol (106-44-5) | LD$_{50}$ | 344 (mouse) 207 (rat) | 0.005%* |
| Emodin (518-82-1) | LD$_{50}$ | 1,000 (rat) | 0.004%* |
| Enterolactone (78473-71-9) | N/A | N/A | 0.074%* |
| Scopoletin (92-61-5) | LD$_{50}$ | 3,800 (rat) | 0.0004%* |
| 3 hydroxyisonicotinic acid (10128-71-9) | N/A | N/A | 0.005%* |
| (6) a amino omega caprolactam (21568-87-6) | N/A | N/A | 0.028%* |
| 4 hydroxycyclohexylcarboxylic acid (17419-81-7) | N/A | N/A | 0.003%* |
| 4 chlorobenzoic acid (74-11-3) | LD$_{50}$ | 1,170 (rat) 1,170 (mouse) | 0.001%* |
| Dibutyl sulfosuccinate (120-36-7) | N/A | N/A | 0.002%* |
| Diethyl phosphate (598-02-7) | LD$_{50}$ | >250 (rat) | 0.001%* |
| Trimethylamine N oxide (1184-78-7) | PDD | 40 (rat) | .000907 |
| Indole 3 acetic acid (87-51-4) | LD$_{50}$ | >500 (rat) 1,000 (deer mouse) | .00016 |
| Dichloroacetic acid (79-43-6) | LD$_{50}$ | 2,820 (rat) | 0.195718 |

| Heavy Metals | | | | |
|---|---|---|---|---|
| Chemical | Method | LD50 (animal model) | Reported Value | Normalized Amount (mg/50 mg cap) |
| Arsenic | AOAC 993.14 | oral toxicity 763 mg/kg (rat) oral toxicity 145 mg/kg (mouse) | 128 ppb | 0.0000064 mg/cap |
| Cadmium | AOAC 993.14 | oral toxicity 2,330 mg/kg (rat) | 373 ppb | 0.0000186 mg/cap |
| Lead | AOAC 993.14 | See note. | 216 ppb | 0.0000108 mg/cap |
| Methyl mercury | AOAC 993.14 | oral toxicity 29.9 mg/kg (rat) oral toxicity 57.6 mg/kg (mice) oral toxicity 71 mg/kg (guinea pig) | 18.8 ppb | 0.0000009 mg/cap |
| Pesticides and Herbicides | | | | |
| Glyphosate | (Tseng et al., 2004) | oral toxicity >2000 mg/kg (rat) | 0.21 mg/kg | 0.0000105 mg/cap |
| Pesticide and herbicide residues | AOAC 2007.01 | | None detected at LOQ | N/A |
| Environmental Contaminants | | | | |
| Bismuth | AOAC 2011.19 and 993.14 (modified) | oral toxicity > 2000 mg/kg (rat) NOAEL 1000 mg/kg (rat) | 117 ppb | 0.0000058 mg/cap |
| Bisphenol A (BPA) | AOAC 2007.01 Modified | | <1.0 µg/kg | <0.00000000005 mg/cap |
| Naturally occurring chemicals | | | | |
| Acrylamide | FDA Method Acrylamide rpc2003 | 0.6 mg/kg | 494 µg/kg | 0.0000000247 mg/cap |

| Test | Detection/Count | Comments |
|---|---|---|
| Total Aerobic Microbial Suitability | Pass | |
| Total Aerobic Microbial Count | <100 cfu/g | |
| Total Combined Mold/Yeast Suitability | Pass | |
| Total Combined Yeasts/Moulds Count | <100 cfu/g | |
| Candida albicans Suitability | Pass | |
| Candida albicans Detection | Not detected | |
| Clostridium spp. Suitability | Pass | |
| Clostridium spp. Detection | Not detected | |
| Escherichia coli Suitability | Pass | |
| Escherichia coli Detection | Not detected | |
| Pseudomonas aeruginosa Suitability | Pass | |
| Pseudomonas aeruginosa Detection | Not detected | |
| Salmonella spp. Suitability | Pass | |
| Salmonella spp. Detection | Not detected | |
| Staphylococcus aureus Suitability | Pass | |
| Staphylococcus aureus Detection | Not detected | |
| Bile Tolerant Gram Negative Bacteria Suitability | Pass | |
| Bile Tolerant Gram Negative Bacteria Detection | Detected | |
| Bile Tolerant Gram Negative Bacteria Detection semi quant | <10 MPN | Acceptable level |

*FIG. 10*

COMPOSITION OF MATTER AND METHODS FOR A FECAL-DERIVED STERILIZED PREBIOTIC AND POSTBIOTIC

CROSS-REFERENCE TO RELATED APPLICATIONS

This application is a continuation in part of international application Serial No. PCT/US20/56131, filed on Oct. 16, 2020, and titled "FECAL-DERIVED STERILE POSTBIOTIC COMPOSITION AND METHOD THEREFOR," which claims priority to U.S. provisional application No. 62/923,174, filed on Oct. 18, 2019, both of which are incorporated by reference herein in their entirety. This application also claims the benefit of priority of U.S. Provisional Patent Application Ser. No. 63/178,468, filed on Apr. 22, 2021, and titled "FECAL-DERIVED STERILE PREBIOTIC AND POSTBIOTIC COMPOSITION AND METHOD THEREFOR," which is incorporated by reference herein in its entirety.

FIELD OF THE INVENTION

The present invention generally relates to the field of prebiotics and postbiotics. In particular, the present invention is directed to a composition of matter and methods for a fecal-derived sterilized prebiotic and postbiotic.

BACKGROUND

Large scale clinical research specifically designed to address safety and tolerability of non-sterilized fecal microbiota transplant (FMT) in healthy populations has been lacking, which may be in part due to the financial burden of these studies and to the speed with which the non-sterilized FMT was introduced. However, the noticeable efficacy of non-sterilized FMT in treating Clostridioides *difficile* infections and related conditions allowed non-sterilized FMT to propel forward in a non-traditional drug pipeline as an investigational new drug (IND) for disease states.

SUMMARY OF THE DISCLOSURE

In an aspect, a composition for a fecal-derived sterilized prebiotic and postbiotic is illustrated. The composition comprises a plurality of biological macromolecules including at least short chain fatty acids and a plurality of agents. The short chain fatty acids include acetic acid, propionic acid, and butyric acid.

In another aspect, a manufacturing method for making a composition for a fecal-derived sterilized prebiotic and postbiotic is shown. The method comprises collecting a stool sample from a healthy, screened donor, wherein the stool sample is frozen, sterilizing the stool sample, blending the stool sample with a liquid to create a fecal-derived composition, and stabilizing the fecal-derived composition by lyophilization.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 3 is a table representing an exemplary average total weight of the plurality of biological macromolecules in an exemplary embodiment of a composition;

FIG. 6 is an exemplary table showing short chain fatty acid changes in stool samples from increasing the pH using sodium hydroxide;

FIGS. 7A, 7B, and 7C are exemplary tables representing the breakdown of major biological macromolecules measured in a composition;

FIG. 8 is an exemplary embodiment of the detection and quantification results of a list of potentially harmful compounds found in a composition;

FIG. 9 is an exemplary embodiment of a table showing toxicology testing results of a composition;

FIG. 10 is an exemplary embodiment of a table showing possible microbiological tests to be performed on a freshly autoclaved stool sample;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to a composition of matter and methods for a fecal-derived sterilized prebiotic and postbiotic. Aspects of the present disclosure may include the composition including a plurality of biological macromolecules. Aspects of the present disclosure may include the plurality of biological macromolecules including at least a short chain fatty acid. Aspects of the present disclosure may include the short chain fatty acids including acetic acid, propionic acid, and butyric acid. Aspects of the present disclosure may further include the composition comprising a plurality of agents. Aspects of the present disclosure may include the plurality of agents including at least a co-emulsifying agent.

For various medical reasons, it may be desirable to deliver healthy human stool and/or postbiotics extracted from stool to a recipient. The delivery of healthy human-derived stool to the colon of a recipient patient is generally known as fecal microbiota transplantation, microbial transfer therapy, or fecal transplant. In recent years, the transplant of healthy, live microbiota to a recipient has been useful for treating recurrent and/or antibiotic resistant infections.

The composition described herein involves a fecal-derived postbiotic product (also referred to herein as "FSP"). A FSP composition or extract is sterilized to exclude any live organisms (including bacteria, archaea, fungi, parasites, protozoa, and viruses). Also described herein are methods of using sterilized FSP compositions. Sterilized FSP and lyophilized sterilized FSP can be used to formulate various products. Dosages of each respectively can be about 0.25 milliliters to about 15 milliliters per day and about 10 milligrams to about 5 grams per day of a lyophilized FSP per subject. The sterilized FSP and lyophilized sterilized FSP can be formulated as appropriate for administration orally, intranasally, vaginally, rectally, or topically. The sterilized FSP and lyophilized sterilized FSP can be formulated into a capsule, soft gel, tablet, pill, gel, lotion, liquid or syrup, suppository, powder, mouthwash, and paste for purposes of administration.

Figure 1:
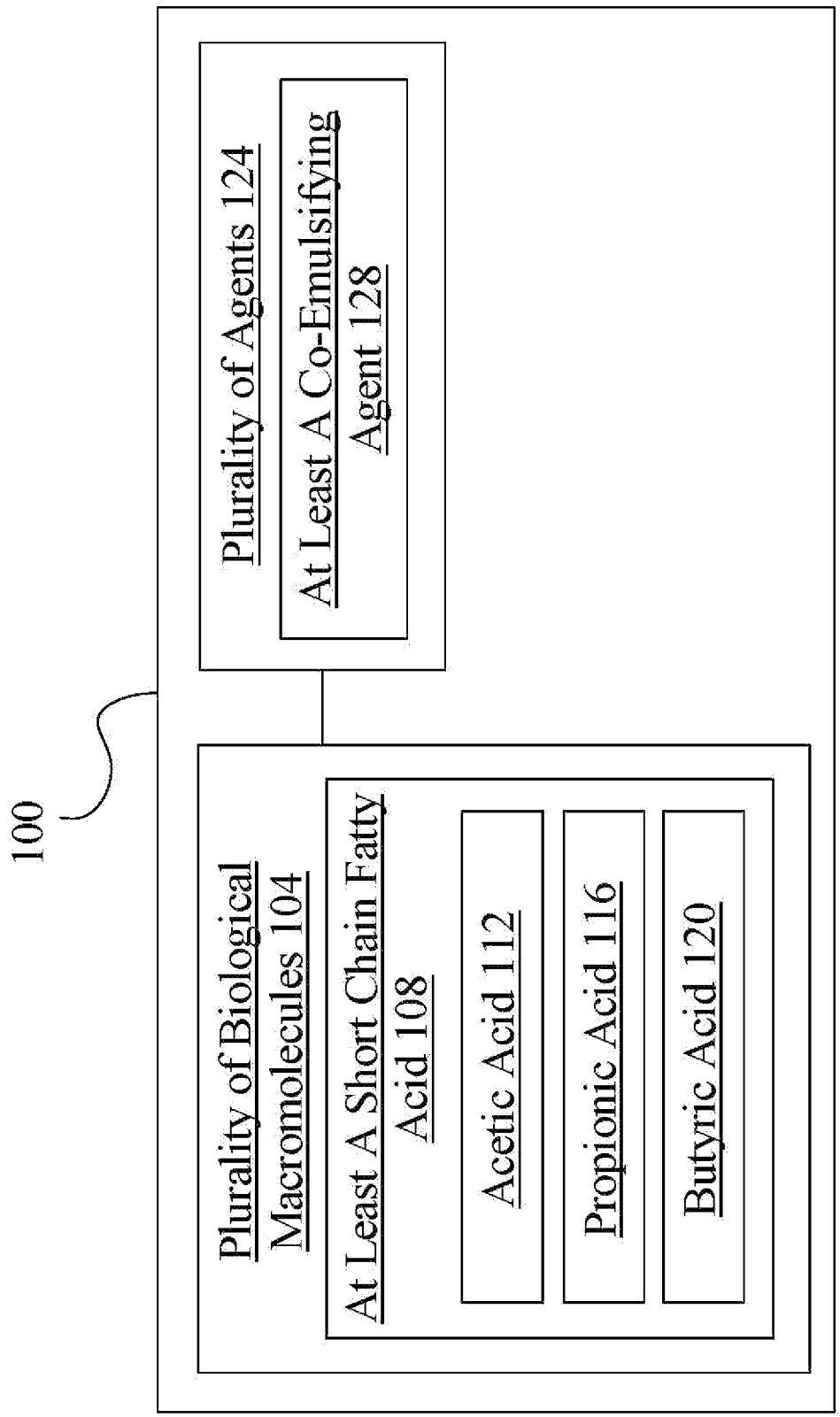
FIG. 1 is a block diagram illustrating an exemplary embodiment of a composition of matter for a fecal-derived sterilized prebiotic and postbiotic.

Now referring to FIG. 1, a block diagram illustrating an exemplary embodiment of a composition 100 of matter for a fecal-derived sterilized prebiotic and postbiotic is presented. Although for the sake of clarity individual elements of a composition are depicted separately, elements may be blended or otherwise intermingled together. As used herein, a "postbiotic" is a sterilized fecal-derived postbiotic composition or product containing said composition that includes bacterial biological macromolecules 104, cellular components of one or more killed bacteria, viruses, fungi, archaea, food byproducts, as well as donor-derived molecules. Short chain fatty acids (SCFAs) are an example of a primary bacterial metabolite. As used in this disclosure, a "metabolite" is a small molecule that is the intermediate or end product of metabolism and is further explained herein with reference to FIG. 4. Also as used herein, a "prebiotic" can include prebiotic dietary fibers, bacteria, yeasts, or the like that are beneficial to the subject to which they are administered. In other words, prebiotics are the fiber or the food for beneficial bacteria and/or other microorganisms in a human or animal digestive tract. Also as used herein, "postbiotics" are the chemicals released from microorganisms that live in a human or animal digestive tract when they metabolize precursor molecules originating from the host or from ingested foods. Composition 100 may be either a prebiotic and/or a postbiotic. Composition 100 is "fecal-derived", meaning it includes, but is not limited to, proteins, undigested food residues, polysaccharides, and microbial biomass. However, composition 100 is "sterilized" because it is free from bacteria or other living microorganisms. The process of sterilization is further explained herein with reference to FIG. 14.

Still referring to FIG. 1, composition 100 includes a plurality of biological macromolecules 104. In this disclosure, a "biological macromolecule" is a molecule, such as a nucleic acid, protein, carbohydrate, and/or lipid, with a relatively large molecular weight. Plurality of biological macromolecules 104 may comprise bile acids; a "bile acid" is an acid made by the liver that is important for the digestion and absorption of fats. Plurality of biological macromolecules 104 may comprise amino acid derivatives. In this disclosure, "amino acid derivatives" are amino acid molecules that have had a reaction at the amino, carboxy, or side-chain functional groups or has had a hydrogen atom replaced by another heteroatom. Plurality of biological macromolecules 104 may further comprise ceramides. A "ceramide" is a waxy lipid molecule found in cell membranes and composed of sphingosine and a fatty acid. Additionally, plurality of biological macromolecules 104 may further comprise lipopolysaccharides, which are large molecules consisting of a lipid and a polysaccharide composed of O-antigen, outer core and inner core joined by a covalent bond. Furthermore, plurality of biological macromolecules 104 may further comprise capsular polysaccharides. "Capsular polysaccharides" are highly hydrated molecules linked to a cell surface via covalent bonds to phospholipids. Lastly, plurality of biological macromolecules 104 may also include sphingosines, which are unsaturated, long-chain amino alcohols usually found in cell membranes. One or more of any of the biological macromolecules described above may be included in plurality of biological macromolecules 104. Examples of biological macromolecules may include, but without limitation, chenodeoxycholic acid, linoleic acid, deoxycholic acid, alanine, leucine, indole derivatives, palmitic acid, sugars, cis-vaccenic acid, 10-hydroxystearate, xenobiotics, nucleotides, or the like.

With continued reference to FIG. 1, plurality of macromolecules 104 may include a sugar. A "sugar" as used in this disclosure, is one or more carbohydrates. A sugar may include a monosaccharide, a disaccharide, and/or an oligosaccharide. For example a sugar may include glucose, fructose, galactose, sucrose, lactose, maltose and the like. Plurality of macromolecules 104 may include an amino acid. An "amino acid" as used in this disclosure, is an organic compound that contains an amino and carboxylate functional group along with a side chain specific to each particular amino acid. For instance and without limitation, an amino acid may include histidine, isoleucine, leucine, lysine, methionine, phenylalanine, tryptophan, valine and the like. Plurality of macromolecules 104 may include a cofactor. A "cofactor" as used in this disclosure is a substance that aids in the activity of an enzyme. A cofactor may be a helper molecule that may assist in biochemical transformation. A cofactor may include an organic cofactor. For example, an organic cofactor may include a vitamin and/or vitamin derivative such as thiamine pyrophosphate, NAD*, pyridoxal phosphate, methylcobalamin, biotin, Coenzyme A, ascorbic acid, menaquinone, flavin mononucleotide, and the like. In yet another non-limiting example, an organic cofactor may include a non-vitamin derivative such as adenosine triphosphate, S-Adenosyl methionine, Coenzyme B, Coenzyme M, Coenzyme Q, glutathione, heme, lipoamine, methanofuran, molybdopterin, nucleotide sugar, tetrahydrobioptrin and the like. A cofactor may include an inorganic cofactor. For example, an inorganic cofactor may include a metal ion such as iron, magnesium, manganese, cobalt, copper, zinc, molybdenum and the like. Plurality of macromolecules 104 may include a vitamin. A "vitamin" as used in this disclosure, is an organic molecule that is a micronutrient needed for functioning of an organism. A vitamin may be unable to be synthetized in sufficient amounts by an organism. A vitamin may include a mineral. For instance and without limitation, a vitamin may include Vitamin A, Vitamin D, Vitamin E, Vitamin K, Vitamin C, Vitamin B6, Vitamin B12, folate, iodine, copper, zinc, and the like. Plurality of macromolecules 104 may include a preserving agent. A "preserving agent" as used in this disclosure, is any substance that may aid in extending the shelf life and/or prevent undesirable chemical change of composition 100. A preserving agent may include an antimicrobial preservative such as sorbic acid, benzoic acid, parabens, sulfur dioxide, sulfites, nitrites, nitrates, lactic acid, propionic acid, phosphoric acid, formaldehyde and the like. A preserving agent may include an antioxidant such as but not limited to ascorbic acid, sodium ascorbate, butylated hydroxytoluene, gallic acid, sulfur dioxide, tocopherols and the like.

Continuing to refer to FIG. 1, plurality of biological macromolecules 104 include at least a short chain fatty acid 108. In this disclosure, a "short chain fatty acid" is a fatty acid molecule with fewer than six carbon atoms. SCFAs represent a primary energy source for human or animal colonocytes, and as a result are important for gastrointestinal health. At least a short chain fatty acid 108 may be considered a postbiotic, as described above, and may be produced by beneficial bacteria in a microbiome from carbohydrates and prebiotic dietary fibers. However, production of at least a short chain fatty acid 108 may be limited if the host does not consume enough plant-based foods or fiber or if certain SCFA-producing strains of bacteria are missing or deficient. Examples of at least a short chain fatty acid 108 may be, without limitation, formic acid, acetic acid, propionic acid, butyric acid, isobutyric acid, valeric acid, and isovaleric acid, some of which are further explained below. At least a short chain fatty acid 108 may be in salt formation. In this disclosure, "salt formation" refers to a form of acid that produces an acidic solution after dissolving in water. Acids may transform into salt formation when neutralized by metal carbonates. Also, at least a short chain fatty acid 108 may be in ester formation, which refers to a chemical compound derived from an acid in which at least one carboxyl group is replaced with a hydrocarbon group. Ester formation may occur as a function of a chemical reaction between carboxylic acids and alcohol. Any form of any of the at least a short chain fatty acids 108 explained above may be used in composition 100.

Still referring to FIG. 1, at least a short chain fatty acid 108 includes acetic acid 112. In this disclosure, "acetic acid" is a type of short chain fatty acid chemical compound that is the byproduct of fermentation. Acetic acid 112 is a type of carboxylic acid. Acetic acid 112 may be in either salt or ester formation, as explained above. Acetic acid 112 may also be in liquid form. At least a short chain fatty acid 108 also includes propionic acid 116. A "propionic acid" is, in this disclosure, a naturally occurring carboxylic acid. Propionic acid 116 may be referred to as propionate or propanoate in its salt and ester formations, respectively. In addition, propionic acid 116 may be produced industrially by hydrocarboxylation of ethylene and may be miscible in water. At least a short chain fatty acid 108 includes butyric acid 120. As used in this disclosure, "butyric acid" is a straight-chain carboxylic acid created by obligate anaerobic bacteria in the colon as a byproduct of anaerobic fermentation. Butyric acid 120 may be an oily, colorless liquid with an unpleasant odor, or could be in salt and ester formation as well. Butyric acid 120 is a common industrial chemical and does not occur widely in nature.

In composition 100, the amount each of the above short chain fatty acids is represented by a specified ratio by weight. A "ratio by weight" is a comparison of equal weights inside the composition, rather than by amount. Composition 100 may comprise a ratio by weight between acetic acid 112, propionic acid 116, and butyric acid 120, in which the ratio by weight may be within a range of 60±10:20±10:20±10, respectively.

Short chain fatty acids may be produced as an end-product of anaerobic fermentation of complex carbohydrates by the microbiota in the colon. Acetic acid 112 and butyric acid 120, explained below, may be essential or healthy human physiology because they are a primary energy source for colonocytes. Propionic acid, the other most abundant short chain fatty acid, is utilized in the liver as a substrate for glucose production. Acetic acid, butyric acid and propionic acid can be generally represented in a ratio of 60:20:20. Short chain fatty acids have also been shown to interact with a wide array of human cells and impact the immune system and metabolism throughout the body via G protein-coupled receptors (GPCRs). In addition, butyric acid 120 has been shown to act as a histone deacetylase inhibitor which impacts the epigenetics of human cells independent of GPCR signaling. These important postbiotic molecules may not only be conserved from the stool product throughout the process described herein, but their concentrations are slightly increased after the sterilization process step of autoclaving. Valerate is also an important short chain fatty acid and is maintained at an estimated concentration of 38 µg/g in the sterilized lyophilized FSP product compared to concentrations of 18-45 µg/g valerate obtained using a traditional FMT procedure.

Still referring to FIG. 1, another class of biological macromolecules present in postbiotics may be bile acids. There is evidence that several secondary bile acids, including the ones identified using metabolomics analysis in the composition, act as immunomodulators that can induce T regulatory cells instead of Th17. The secondary bile acid, ursodeoxycholic acid (UDCA), has long been used in the treatment of liver disease. Several synthetic bile acids are pipeline blockbuster drugs for NASH and NAFLD. Taurodeoxycholic acid (TDCA) is another secondary bile acid that has been shown to impact immune function. The sterilization and lyophilization method disclosed herein maintain the composition of secondary bile acids and reveal a significantly increased concentration of taurodeoxycholate specifically.

Another biological macromolecule that may be present in the sterilized FSP products are amino acid derivatives or tryptophan metabolites. Tryptophan metabolites have been studied for their role in neuroimmunomodulation and inflammatory signaling. Indole derivatives have been shown to bind the aryl hydrocarbon receptor which has a broad array of functions including impacting immune activation. Indole-3-propionic acid contributes to remission through an IL-10 mediated immune pathway in human and mouse models of colitis. This class of molecules is conserved in the sterilization method described herein.

Still referring to FIG. 1, composition 100 further includes a plurality of agents 124. In this disclosure, "agent" refers to a chemical compound substance that exerts some sort of force or effect for a specific purpose. In other words, a plurality of agents 124 are a plurality of substances capable of producing a specific effect. For example, but without limitation, skin irritation may be a resultant of skin contact with some sort of degreasing agents. Moreover, plurality of agents 124 may include a screening agent. Plurality of agents 124 may also include a vitamin. Plurality of agents 124 may also include an essential oil. Plurality of agents 124 may further include a plant protein. Plurality of agents 124 may also include an anti-oxidizing agent. Plurality of agents 124 may also include a preserving agent. Plurality of agents 124 may include a fragrance. Plurality of agents 124 may also include a ceramide. Plurality of agents 124 may further include a moisturizing agent. Plurality of agents 124 may include a lubricating agent. Plurality of agents 124 may also include a polysaccharide. Plurality of agents 124 may also include a filler. Other types of agents may include, without limitation, dust, pollen, cement, asbestos, benzene, or the like. Plurality of agents 124 may be any chemical substance that impacts another.

Still referring to FIG. 1, plurality of agents 124 comprises at least a co-emulsifying agent 128. A "co-emulsifying agent" is a type of chemical compound that permits the mixing of two or more liquids. At least a co-emulsifying agent 128 may also keep the mixture together and prevent the two or more liquids from separating. At least a co-emulsifying agent 128 may be referred to as a "co-emulsifier" and helps mix compounds in composition 100. As an example, without limitation, at least a co-emulsifying agent 128 may help mix oil and water together and keep it together as a mixture without separation. At least a co-emulsifying agent 128 may include cetyl alcohol. At least a co-emulsifying agent 128 may also include stearyl alcohol. At least a co-emulsifying agent 128 may also include octacosanol. At least a co-emulsifying agent 128 may further include palmitic acid. At least a co-emulsifying agent 128 may include stearic acid. Additionally, at least a co-emulsifying agent 128 may also include surfactants, which are agents that work by lowering the surface tension of different liquids. At least a co-emulsifying agent 128 may also include monoglycerides, diglycerides, polyoxethylene derivatives, egg yolk, diacetyl tartaric acid esters of monoglycerides (DATEM), polyglycerol ester (PGE), sorbitan ester (SOE) and PG ester (PGME).

Referring still to FIG. 1, composition 100 may come in any dosage form, including for example a solid or liquid form. Composition 100 may be in the form of a solid, such as a pill, a capsule, a tablet, a paste, or a powder. Composition 100 may be in the form of a liquid, such as an aerosol, a gel, a lotion, a liquid, a body wash, or the like. In any form, composition 100 is meant to be consumed, ingested, injected, inserted and/or applied topically by the host to enact the benefits of composition 100.

Furthermore, and still referring to FIG. 1, composition 100 may be admixed with a non-sterilized fecal composition. In this disclosure, a "non-sterilized fecal composition" is a composition derived from human feces that has yet been sterilized. When sterilized and combined with other materials, a non-sterilized fecal composition may have many health benefits when consumed by a human host. Composition 100 may also be admixed with a probiotic, a live biotherapeutic, or a synthetic microbial community. As used herein, a "live biotherapeutic" or "LBT" is a biological product that contains live microorganisms such as bacteria and/or yeast that are naturally occurring, recombinant, or clonally selected and when administered to the subject confer a health benefit to the subject, a synthetic microbial community, or a non-sterilized fecal composition Adding FSP with LBTs may be used to augment the growth of bacteria once administered to the recipient. Probiotics can be in the form of capsule as supplements or in foods, like yogurt. *Lactobacillus* spp. are examples of common probiotic species as are *Bifidobacterium* spp., and *Saccharomyces boulardii*. On the other hand, as used herein a "synthetic community" and a "synthetic microbial community" are the construction of a microbial system that is simplified and not found in nature. Once admixed together, the fecal composition may then be sterilized, a process that is further explained herein with reference to FIG. 14.

Figure 2:
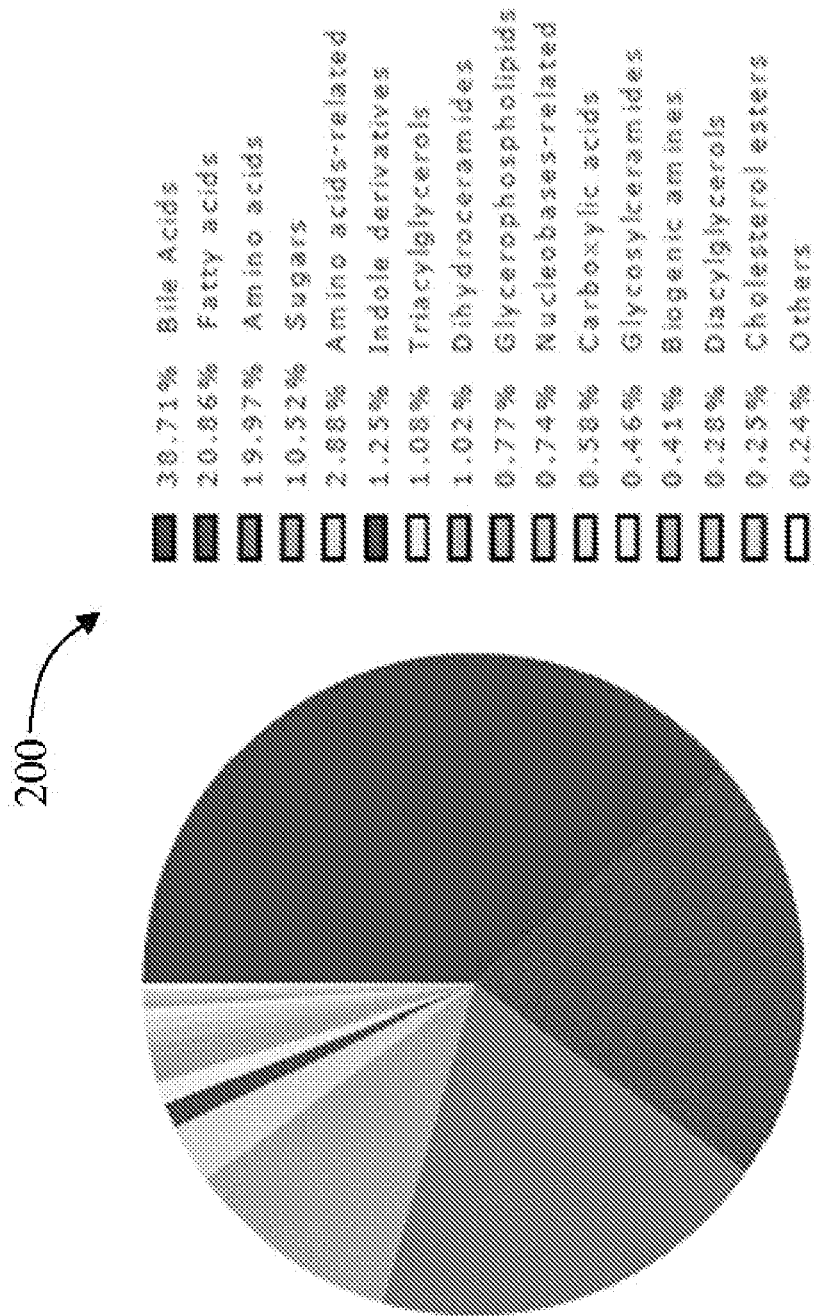
FIG. 2 is a pie chart representing an exemplary percentage breakdown by the total weight of the plurality of biological macromolecules in an exemplary embodiment of a composition.

Now referring to FIG. 2, a pie chart representing an exemplary percentage breakdown by the total weight of the plurality of biological macromolecules 104 in the composition is shown. Plurality of biological macromolecules 104 of composition 100 represent around 20-30% of weight per gram of dried, lyophilized product. Composition 100 overall may be composed of water and lipid-soluble, biological macromolecules, including microbially-derived postbiotics such as secondary bile acids and short-chain fatty acids (SCFAs) as described above. In general, it is composed of bile acids, amino acids, glucose, short chain fatty acids, long and medium-chain fatty acids, polyunsaturated fatty acids, branched fatty acids, modified amino acids, indole derivatives, acylglycerols, ceramides, phospholipids, nucleic acids, carboxylic acids, biogenic amines, cholesterol esters, vitamin derivatives, carnitines, alkaloids, sphingolipids, and other endogenously produced small molecules. The figure itself is an actual percentage breakdown by the total weight of all major biological macromolecules measured from two separate masterbatches of the fecal derived composition analyzed in triplicate on the targeted MxP Quant500 LC-MS/MS assay.

Now referring to FIG. 3, a table representing an exemplary average total weight of the plurality of biological macromolecules in the composition is illustrated. An exemplary total weight in micrograms per 50-milligram capsule is exemplified, meaning that there is that many micrograms of that specific biological macromolecule in a 50-milligram capsule of composition 100. The table represents the average total weight by biochemical from two separate masterbatches of the fecal derived composition analyzed in triplicate on the targeted MxP Quant500 LC-MS/MS assay, as stated above.

Figure 4:
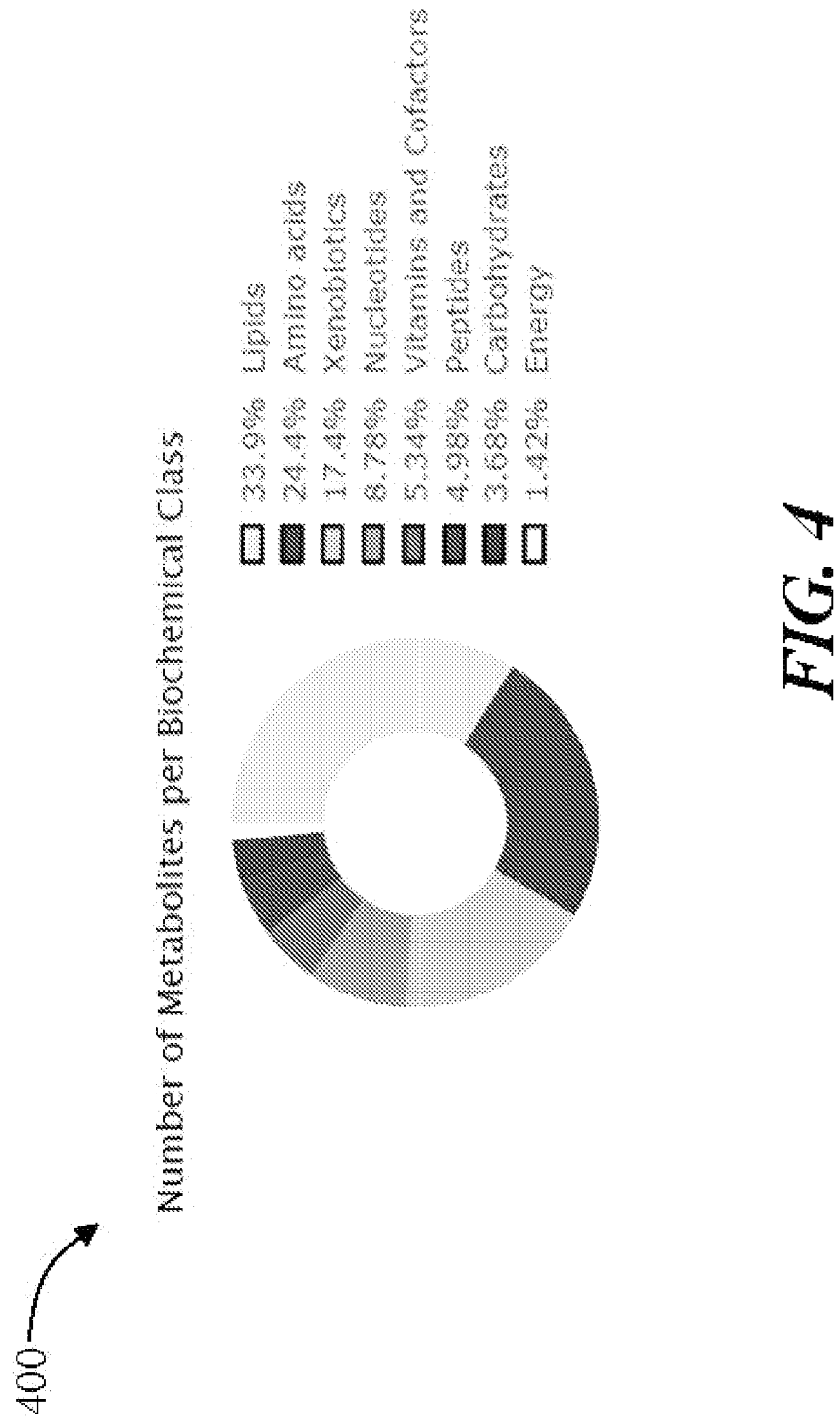
FIG. 4 is a pie chart representing the total number of metabolites identified in the plurality of biological macromolecules in an exemplary embodiment of a composition.

Now referring to FIG. 4, exemplified is a pie chart representing the total number of metabolites identified in the plurality of biological macromolecules in an exemplary embodiment of composition 100. As previously stated, metabolites are small molecules used in metabolism. Short chain fatty acids may be categorized as essential microbiome-derived metabolites for normal colonocyte function. Metabolites may also be referred to herein as postbiotics. To identify such molecules in composition 100, both untargeted and targeted analytical mass spectrometry methods may be used, such as liquid chromatography electrochemical-array mass spectrometry (LC-EC-array-MS). In the figure, the metabolites listed are those most known biochemical classes commonly found in human stool, while the percentages correlate to the total amount of individual molecules identified by class. It is important to note that each stool sample coming from a different person will vary in the percentages of metabolites.

Figure 5:
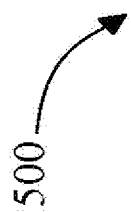
FIG. 5 is an exemplary chart of quantitative results from two donors.

Now referring to FIG. 5, shown is an exemplary chart of quantitative results from two possible donors. While an untargeted analytical mass spectrometry method may allow for clearer initial characterization of composition 100, it may not accurately quantify the microbial metabolites found in the stool. Because of this, a separate, targeted LC-MS/MS assay may be performed to quantify the amount of short chain fatty acids present in individual donors' stools after being processed into composition 100. In the table, each sample represents a separate stool prepared as an individual batch of composition 100; the table lists the quantified amounts of short chain fatty acids detected by LC-MS/MS and show that the primary short chain fatty acids in our donors' processed samples is acetate, propionate, and butyrate, which are explained in detail herein.

Now referring to FIG. 6, an exemplary table showing short chain fatty acid changes in stool samples from increasing pH using sodium hydroxide (NaOH). Quantitative changes in short chain fatty acid amounts may occur when stool samples experience chemical processes, such as increasing pH. As shown in the figure, a pH of 9.0 had the highest short chain fatty acid retention even while undergoing lyophilization. The "FSP-L pH 6.0/7.2/9.0"-labeled columns display an actual concentration measured of lyophilized product in micrograms per gram (µg/g), followed by the preserved amount from the raw stool sample, also known as a baseline, displayed as a percentage of the raw stool sample, followed by the preserved amount from the sterilized sample, which is displayed in the table as "% FSP". The metabolites in the stool sample are volatile, so increasing the pH of the solution post-sterilization may conserve more of the short chain fatty acids during the freeze-drying process.

Figures 7B, 7C:
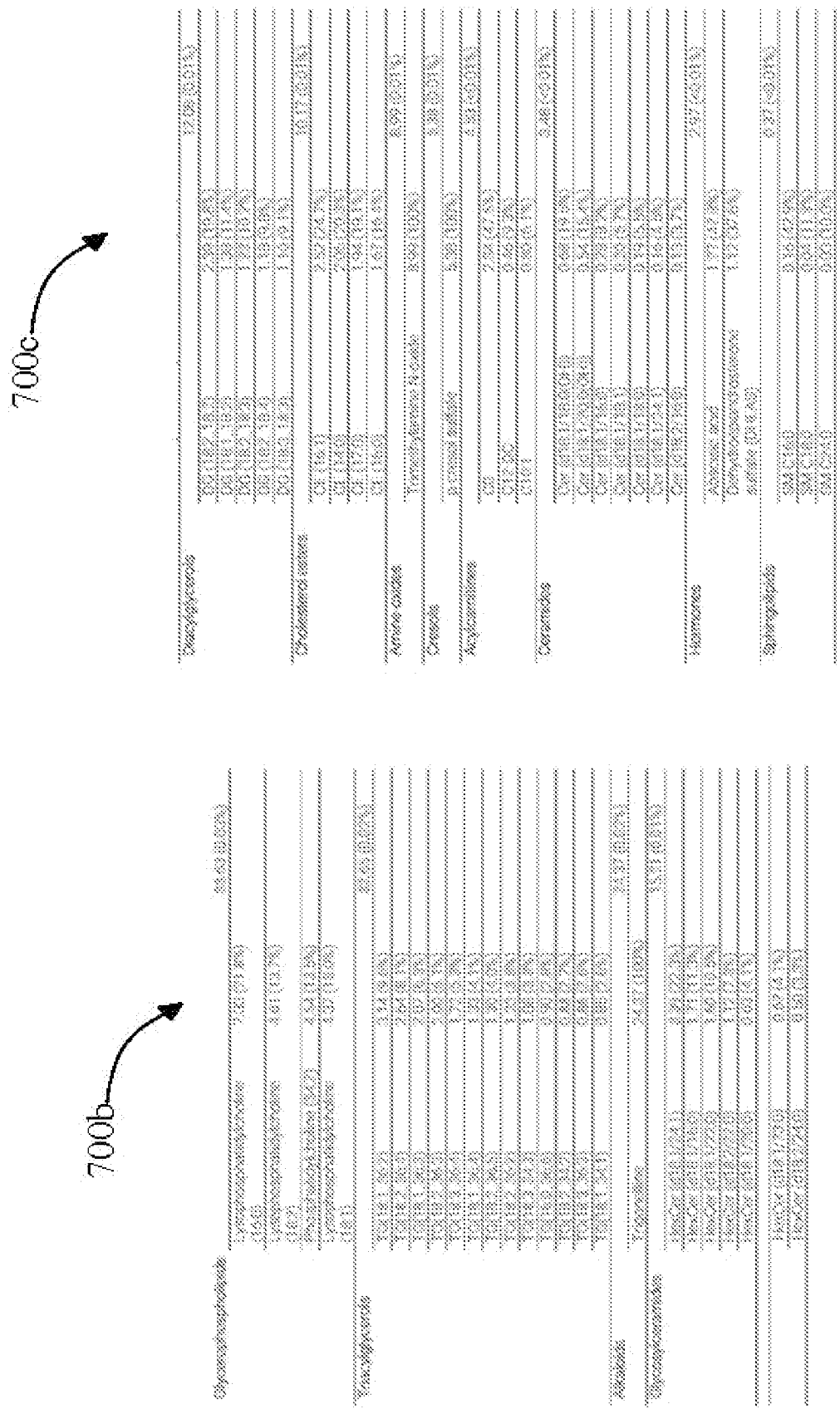

Now referring to FIGS. 7A, 7B, and 7C, the table shown is an exemplary breakdown of the major biological macromolecules measured in composition 100. Of the 624 metabolites measured by, in this disclosure, a MxP Quant 500 kit, an average of 383 metabolites were above the limit of detection in composition 100, as determined by the assay. The table lists the primary metabolites that contribute to each major biochemical class and the average percent of the total class and overall total in picomoles per milligram.

Now referring to FIG. 8, the table is an exemplary embodiment of the detection and quantification results of a list of potentially harmful compounds found in composition 100. The list of identified compounds from both metabolomics assays may be screened against five public toxin databases. However, not all identified and reviewed biological macromolecules hold toxicity value, but those that do require large doses relative to their quantified amount. If the MxP Quant500 kit measured potentially toxic compounds, results may be shown in the final column of the table from two separate batches of stool measured in triplicate. Additionally, further toxicology investigations beyond the metabolomics assays may be performed.

Now referring to FIG. 9, an exemplary embodiment of a table showing toxicology testing results of composition 100. "Toxicology testing" tests the composition to see how harmful it may be to consume. Toxins may include, but without limitation, heavy metals, pesticide and herbicide residues, environmental contaminants, and acrylamides. In this embodiment, all tested heavy metals, pesticides and herbicide residues, environmental contaminants, and acrylamide levels were well below tolerable upper limits.

Now, FIG. 10 is an exemplary embodiment of a table showing possible microbiological tests to be performed on a freshly autoclaved stool sample. This may be done to confirm that autoclaving fecal samples at 121° C. for 30 minutes resulted in a sterilized product. In an embodiment, the stool slurry may be potentially incubated with Tryptic Sot Broth (TSB) media at 20-25° C. for four days and Fluid Thioglycolate Medium (FTM) media at 30-35° C. for 14 days. No growth may be observed in samples inoculated with the stool slurry in either medium to confirm sterilization. Except for bile-tolerant gram-negative bacteria, all mold, yeast, and bacterial tests may pass suitability testing if they are not detected.

Figure 11:
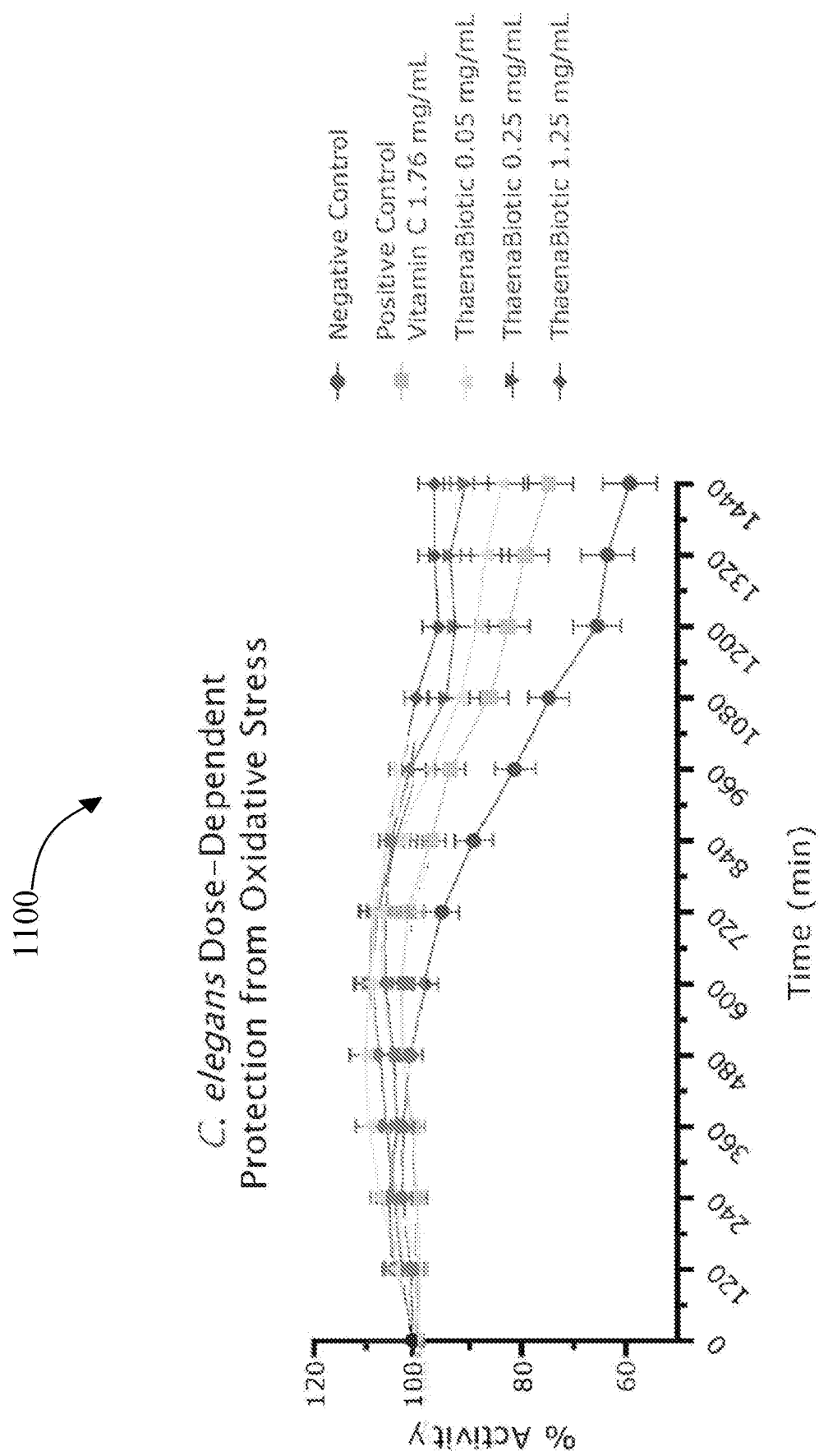
FIG. 11 is an exemplary line graph demonstrating a dose-dependent protective effect when a composition is administered to *C. elegans*.

Now referring to FIG. 11, the figure shows an exemplary line graph demonstrating a dose-dependent protective effect when composition 100 is administered to C. elegans. In this disclosure, "C. elegans" is used as a model organism to investigate molecular mechanisms influencing aging, behavior, and toxicity. Composition 100 may be administered to C. elegans following exposure to 10 millimeters of paraquat, which is a reactive chemical that induces oxidative stress. As a result, composition 100 demonstrates a dose-dependent protective effect. Once exposed to the paraquat, in an embodiment, composition 100 may be separated into five intervention groups to determine the effect: a negative control group, a Vitamin C positive control group, a 0.05 milligram per milliliter sample group of composition 100, a 0.25 milligram per milliliter sample group of composition 100, and a 1.25 milligram per milliliter sample group of composition 100. Composition 100, as seen in the exemplary chart, may be more protective against oxidative stress then Vitamin C. Furthermore, composition 100 may demonstrate remarkably potent protection against acute physiologic stress induced by oxidative stress.

Figure 12:
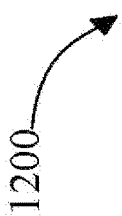
FIG. 12 is a table representing the percentages of biological macromolecules in an exemplary embodiment of the composition.

Now referring to FIG. 12, a table representing percentages of biological macromolecules in an exemplary embodiment of the composition 100 is illustrated. In an embodiment, composition 100 may include a plurality of biological macromolecules comprising, without limitation, amino acids, carbohydrates, cofactors and vitamins, energy, lipids, nucleotide, partially characterized molecules, peptide, fecal matter and xenobiotics. Exemplary percentages by weight are also shown in the figure; percentages may vary by composition. In an embodiment, composition 100 may comprise 19% amino acids, 3% carbohydrates, 4% cofactors and vitamins, 1% energy, 26% lipids, 7% nucleotide, 1% partially characterized molecules, 4% peptide, 22% fecal matter, and 13% xenobiotics.

Figure 13:
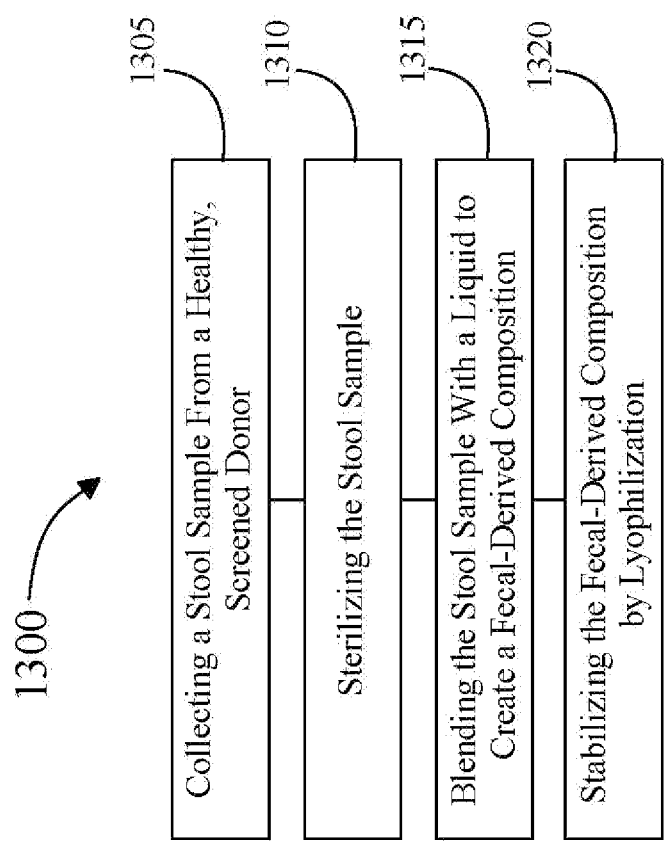
FIG. 13 is a flow diagram illustrating an exemplary embodiment of a manufacturing method for a composition of matter for a fecal-derived sterilized prebiotic and postbiotic.

Now referring to FIG. 13, shown is a flow diagram illustrating an exemplary embodiment of a manufacturing method 1300 for a composition 100 of matter for a fecal-derived sterilized prebiotic and postbiotic.

Still referring to FIG. 13, at step 1305, method 1300 includes collecting a stool sample from a healthy, screened donor, wherein the stool sample is frozen. In this disclosure, a "stool sample" is non-sterilized human fecal matter, while the "donor" is the human person the fecal matter comes from. Stool sample may be considered a non-sterilized fecal composition, as explained above. "Frozen" may include the sample being kept at a temperature of between −20 to −80 degrees Celsius for anywhere from 1-10 years. Healthy, screened donors may experience onboarding and routine testing prior to giving the stool sample. A suitable stool donor may be identified using a fecal transplant questionnaire. If the responses meet qualifications additional screening may be performed. Additional screening may include questioning the potential donor in an interview regarding the answers to the questionnaire, obtaining basic health history, or health practices. Potential donors may be "screened" for any presence of infectious disease symptoms and may provide a stool and serum sample for analysis. Potential donor's serum can be obtained to assess for the presence of an HIV strain or for syphilis for example. HIV and syphilis can be retested after three weeks from the initial testing to check and confirm the absence of seroconversion. All serum and stool laboratory testing may be performed by a qualified laboratory. Additionally, stool analysis may include analysis to detect the presence of six Multi-Drug Resistant Organism genes. Testing may be performed in a stepwise manner. In one aspect, stool assessment may be done in less than 14 days. Upon receipt of assessment, if deemed qualified, potential donors are further screened based on a serum sample and provided perianal swabs for both MRSA and CRE. Serum and stool testing may be performed using a certified laboratory. Additional seroconversion studies for the presence of human immunodeficiency virus (HIV) and syphilis may be performed three weeks after initial screening and before release of a donor's fecal material. Donor stool may not be used for capsule production until this information is obtained and confirmed. Overall, the screening determined whether or not the donor is healthy enough to provide the actual stool sample to be used for composition 100. Generally, this pre-donation screening may help ascertain that a potential donor is free from the following non-exhaustive list of afflictions: chronic disease, autoimmune disease, current or past chronic gastrointestinal disease, atopic asthma, atopic dermatitis, diabetes, metabolic syndrome, mood disorders, chronic pain, and/or infectious diseases. Mood disorders considered for treatment or amelioration of a condition include anxiety, depression and obsessive-compulsive disorder. Individual stool samples from the same healthy, screened donor may be combined after sterilization to form a stool batch. Once formed, the stool batch may be sifted to remove any large particulate matters. Donor screening can be performed using various of the criteria described herein in order to identify a healthy donor.

Still referring to FIG. 13, recruitment of a human donor may begin with a short online survey targeting health-conscious communities. For example, in some embodiments, donors may be recruited from a group of individuals who engage in outdoor activities, eat organic foods, and/or generally live a healthy lifestyle. Key aspects of this survey may identify eligibility of donor to give stool samples. For example, but without limitation, donors may be considered eligible when vaginally birthed and breastfed exclusively for 6 or more months. Additionally, another example may be that the potential donor cannot have been diagnosed with a pre-existing condition, such as the ones described above. A potential donor may then be interviewed regarding the donor's diet and lifestyle. Donor screening may also take into consideration food choices, mental health, and their community or the like. Diet and lifestyle factors may also be considered when selecting donors. In some embodiments, an ideal donor may eat a healthy, well-balanced diet and generally engage in healthful practices that support holistic wellbeing of the individual, such as exercise. If a qualified donor remains active, then the donor may be asked to undergo selected tests every six months or earlier depending on a new exposure or illness. Screening questions may include, without limitation: frequency of bowel movements per day/week, how those bowel movements typically rate on the Bristol stool scale, dietary history, relationship with food, whether the potential donor was born vaginally and/or breast-fed, the environment the potential donor was raised in, number and age of sibling(s), exposure to environmental contaminants, treatment for certain types of infections, history of antibiotic use, weight fluctuations, family health history, characteristics about the potential donor's menstrual cycle (if applicable), age, occupation, weight, height, exercise habits, smoking habits, drinking habits, sexual history, exposure to STIs, illicit drug use, recent tattoo/piercing history, hospitalization, surgery history, medical diagnosis history, mental health, allergies, international travel, prescription and/or supplement use, microbiome history, and more. Donors may also be screened for one or more of the following pathogens or a species falling within bacterial pathogens, parasites, viruses and fungi pathogens, or antibiotic resistant genes.

Still referring to FIG. 13, another screening example for potential donors may include multiple phases. For example, phase 1 of the screening may include an assessment of the donor's serum involving a complete blood count (CBC) with differential, a comprehensive metabolic panel (CMP), a hemoglobin AIC (HgAIC), and antibodies for HIV-1 and HIV-2. Phase I for screening the stool may also include 16s diversity index sequencing, obtaining a metabolomics profile, O&P with giardia antigen, and culturing the stool for the presence of *Salmonella, Shigella, Campylobacter*, and EHEC. Phase 2 of the exemplary screening can occur approximately every six months or after new onset symptoms or a change in risk factors for the donor occurs. Serum at this stage would be tested for CBC with differential and CMP. These phases may or may not immediately follow each other, and phases may be modified as needed. Generally, the frequency and timing of testing will vary depending on the illness or exposure being tested for. HIV and syphilis, for instance, may be retested several weeks after the initial test to check for seroconversion. Follow-up testing for hepatitis B and C may also be useful. No donor stool should be used for powder and/or capsule production until all testing information is complete and confirmed. Some tests may also be repeated every six months throughout the donation time period as an extra safety precaution. Testing may be optional given sterilization of the sterilized fecal-derived postbiotic composition. Additionally, the physical exam portion of the screening may be another phase. An exemplary physical exam list may include, without limitation, as follows: capillary refill, assess for clubbing and peripheral cyanosis, assessment of cranial nerves, inspection of conjunctiva, lips and buccal mucosa, inspection of neck for appearance, symmetry, trachea position, and masses, palpation of the thyroid for enlargement, tenderness and masses, visual assessment of respiratory effort and signs of central cyanosis, lung auscultation, carotid auscultation, cardiac auscultation and palpation, and other similar inspections for the rest of the donor's body.

With continued reference to FIG. 13, although the mental health of a potential donor may be difficult to measure quantitatively, it may be possible to obtain a good sense of the suitability of a potential donor through careful screening of health, personality, and temperament, in addition to asking comprehensive intake questions, performing infectious disease testing, and performing physical examinations. This extensive vetting process may allow a physician to identify potential risk factors associated with a potential donor's lifestyle and overall health. In some embodiments, initial donor screening may be conducted by phone interview to cover basic health history and health practices. If a potential donor passes the phone interview, then a next step in the vetting process may be to follow up with an in-person or remote video interview (e.g., telehealth consult) to review and confirm the potential donor's answers to the intake questionnaire. A next step may then include screening the potential donor for infectious disease, followed by a further step of performing a physical exam on the potential donor, or having them obtain one from their local physician if a remote donor.

Continuing to refer to FIG. 13, once a donor is approved, said donor may receive a set of detailed donor instructions. Donor instructions advise the donor on what to do in order to give stool samples. The instructions may include recommendations for maintaining a healthy microbiome through diet and lifestyle practices. For example, a donor may be instructed to eat an organic, whole foods-based diet that consists of varied fruits and vegetables, and to drink enough water to stay hydrated. A donor optionally may be instructed to engage in body movement each day, which may take the form of housework, gardening, walking, biking, etc. Such movement may be useful in maintaining a healthy microbiome in the donor. Donor instructions may include symptoms that the donor must report as post-screening approval. For example, the donor may be instructed to immediately notify the FMT service provider if the donor experiences any change in bowel habits; sign of cold, flu, or fever; change associated with risk of HIV or hepatitis contraction (e.g., change in sexual practices, blood transfusion, needle stick incidence, new tattoos); use of antibiotics, etc. Donor instructions may also include which types of stool samples are acceptable based on the Bristol Stool Scale or any other suitable stool chart, as well as other information on safe collection, handling, and delivery of stool samples. The donor may also be instructed to avoid contamination of stool with urine, and to notate where the collected stool falls on the Bristol stool scale, along with the date and time of collection. Donor instructions may also include instructions on amount, color, type, etc. of stool sample.

With continued reference to FIG. 13, in some embodiments, once the stool sample is collected, the method may include freezing the stool sample immediately after collection. Freezing may be accomplished in several ways, such as, but not limited to: flash freezing, in a regular freezer, or freeze-drying via sugar crystallization or lyophilization. Freezing of the stool sample may be done at −6° C. to −80° C. The ability to freeze, store, and then transport to then thaw for manufacturing allows for various advantages. Traditionally, non-sterilized FMT may be processed within twelve to twenty-four hours of donation with fresh stool samples. When the live bacteria are the focus of the end-product, this represents an obvious requirement. Stool samples may be selected from multiple donors less than 24 hours before processing, with each donor contributing approximately 2,100 grams of fresh stool. Stools samples may be prioritized for use based on date. Selected stools may be left to thaw at 4 degrees Celsius overnight. Each thawed stool may be opened under a Class IIA biosafety cabinet for the first time since being sealed by the donor at the time of collection and is placed in a self-sealing, glass autoclave vessel. In some embodiments, donors may be required to freeze their own stool samples. Further, by having donors freeze multiple stools at home, not only does this increase convenience in bulk pick-ups, but also may allow a greater donor population geographically. Donors may no longer be limited by location. This method may also provide a decentralization of the stool banks with the capacity for reduced human interaction. In some embodiments, stool samples may be collected, frozen, and couriered on dry ice to a processing location.

Still referring to FIG. 13, composition 100 may provide enhanced safety and efficacy over non-sterilized FMT therapies. As used herein, a "fecal microbiota transplantation (FMT)" is a process of transferring fecal material from one subject to another subject. Non-sterilized fecal microbiota transplant therapy has provided a unique example of how microbial dysbiosis in the gastrointestinal (GI) tract can be improved in order to treat disease. Generally, the transplantation process uses non-autologous fecal matter. The fecal microbiota (or fecal transplant) is generally obtained from a healthy, screened donor, as explained above, and is administered into the colon of a recipient. The process can also be also referred to as microbial transfer therapy, microbiota restoration therapy, intestinal microbiota transfer, donor feces infusion, stool transplant, or fecal bacteriotherapy. As used for the compositions and methods described herein, an FMT product is defined as a fecal pellet derived from a screened donor stool that is processed into a concentrated bacterial pellet. In all instances, "FMT" and "fecal microbiota transplantation" indicate a sample that has not been sterilized and contains live bacteria and viruses. The compositions minimize the risk of transmitting infection from donor stool to a recipient of an FSP capsule or batch of capsules. As with any medical procedure, there are both known and unknown risks associated with non-sterilized FMT. These risks are commonly associated with infectious organisms and/or substances in donor stool that were not identified through screening. Safety concerns regarding infectious disease are particularly worrisome for immunocompromised patients (e.g., patients having AIDS, cancer, diabetes, certain genetic disorders; patients who are malnourished). In addition, the transmission of novel viral and parasitic pathogens, like SARS-COV-2, through live FMT transfer remains of serious concern. FMT remains with risks and potential side effects for the patient receiving the transfer. Much, but not all, of these risks relate to transmitting infection from the donor stool to the recipient. Such risks may be mitigated, but cannot be completely eliminated, even by extensively screening donors prior to stool collection to minimize the risk of exposing the recipient to a known infectious disease or other risk factors. Moreover, a fecal-derived sterilized postbiotic composition as described herein can be used to shift disease states from diseased to healthy when administered to a subject in a therapeutically effective dose. The shift therefore is not linked to a bacterial species-specific mechanism that occurs through the transfer of a live or non-sterilized FMT.

With continued reference to FIG. 13, optionally, once the stool sample is prepared, a tracking protocol may be implemented. For example, a processed stool sample can be given a batch ID number. The ID number may connect each product with its specific processing date, contained in a written database that includes important information, such as, but not limited to the date and time the stool was collected and processed, total volumes of material used, identity of the donor and the processing technician, the specific gram/capsule measurements, and so on. Optionally, the tracking may also comprise a full log of such information for safety and quality control. Additionally, in some embodiments, at least one sterilized fecal composition product from each batch may be saved for quality control tracking. Stool samples may then undergo freezing, thawing, sterilization, and then be freeze-dried such that they are suitable for oral consumption by their intended recipient, as explained further below.

Still referring to FIG. 13, at step 1310, method 1300 includes sterilizing the stool sample. The sterilization step of the methods described herein may be performed prior to blending the stool or after blending the stool or after removal of fiber and particulates, as further explained below. As used herein, the term "sterilize" means to remove or kill all bacteria, viruses, and other living organisms from a sample such as composition 100. Sterilization of the stool sample may kill bacteria and/or viruses while retaining bacterial plurality of biological macromolecules 104. In some embodiments, sterilization may be performed using any of the following non-exhaustive means of sterilization: UV-C light, ozone, sonication, microwave irradiation, pasteurization, autoclaving, tyndallization, steam sterilization, flash sterilization, low-temperature sterilization technologies, filtration, dry-heat sterilization, performic acid, glass bead sterilizer, liquid chemicals, ionizing radiation, gaseous chlorine dioxide, vaporized peracetic acid, infrared radiation and/or any other suitable sterilization technique. In some embodiments, the sterilized fecal product may then be stabilized using a freeze-drying technique also known as lyophilization or cryodesiccation. Sterilization may include the method of autoclaving. In this disclosure, "autoclaving" is a sterilization method that uses high-pressure steam. For example, but without limitation, stool sample may be placed in a chamber, an autoclave, or the like. Temperature and pressure of the chamber is increased to a certain level to create the steam to kill the bacteria and microbes. The step may be performed between about 121 to 134 degrees Celsius for approximately 30 minutes. Autoclaving may also be performed between 135 to 140 degrees Celsius for approximately 20 minutes. The pH of the product may be checked prior to the freeze drying technique, and if the pH is below a specified level, another solution may be added to get the pH to that specified level. For example, if the pH measures 6.0, NaOH may be added to increase the pH from about 6 to about 9.0, or higher than 6.5, or 7.0, or 7.5 or 8.0. By increasing the pH at this stage, improves the ability to maintain short chain fatty acid plurality of biological macromolecules 104 of the sterilized fecal-derived postbiotic during lyophilization. Lyophilization or freeze-drying allows the sterilized fecal product to be preserved in a condensed dry powder that is stable for storage and use at room temperature. The lyophilized sterilized fecal-derived postbiotic powder may then be used for oral, topical, vaginal or rectal intake, intranasal administration, or other formulations for intravenous or parenteral administration as contemplated herein.

With continued reference to FIG. 13, while non-sterilized FMT derived products contain live bacteria, the products and composition 100 described herein may not. The sterilized products, extracts and components derived from the products provide a living-organism free composition that is safe for administration. In one embodiment, it is contemplated that the sterilized fecal derived postbiotic composition described herein can be used as an adjuvant in conjunction with non-sterilized FMT products containing living organisms or synthetic communities of gastrointestinal associated bacteria. The compositions described herein can also be used as a stand-alone composition for administration to treat or ameliorate a condition or in combination with other therapeutics. The sterilized fecal-derived postbiotic composition can normalize an environment in a subject in need thereof by allowing existing bacteria to colonize normally eventually supplanting a disease-associated dysbiotic colonization. The sterilized fecal-derived postbiotic composition described herein is also inherently safer because they eliminate infectious disease risk. This is true for both oral ingestion of the material or topical application. Stool contains bacteria that can overgrow. This overgrowth can cause imbalance in both the gut and on the skin. Bacterial overgrowth on the skin, for example, can cause a topical infection. Sterilization of the fecal-derived postbiotic composition, such as via autoclaving, definitively kills all bacteria and viruses while retaining bacterial plurality of biological macromolecules 104.

Still referring to FIG. 13, at step 1315, method 1300 includes blending the stool sample with a liquid to create a fecal-derived composition. The liquid may include water, such as but not limited to distilled water, water for injection, filtered water, purified water, and/or a buffer and the like. In this disclosure, a "buffer" is an aqueous solution consisting of a mixture of a weak acid and its conjugate base, or vice versa. Its pH, or its acidity, changes very little when a small amount of strong acid or base is added to it, meaning it maintains a constant hydrogen ion concentration. Buffers may be able to neutralize small amounts of added acid or base, thus maintaining the pH of the solution relatively stable. Maintaining the pH of a solution, especially in composition 100, is important because if the pH value of a solution rises or falls too much the short chain fatty acids are volatilized during the lyophilization step. Buffer may include, without limitation, water, a phosphate buffered saline solution, or maldextrin-trehalose solution. Effective ratios of stool to buffer solution may vary, and such variance may depend on the how the stool falls on the Bristol stool scale (or any other such classification system for stool). For example, a blend of approximately 100 grams of stool with approximately 500 milliliters of phosphate-buffered saline (PBS). This 100 gram to 500 milliliters ratio may be suitable for donor stool that is considered to be a "4" on the Bristol stool scale. Other ratios may be more suitable for donor stool that falls elsewhere on the Bristol stool scale. For instance, it may be suitable to add approximately 700 milliliters of buffer solution to 100 grams of donor stool that is classified as a "3" on the Bristol stool scale. In other words, the drier the donor stool is, the greater the amount of buffer solution that may need to be added to the donor stool. After a buffer solution is added to the donor stool in a suitable container, the mixture should be blended to produce a slurry, or semiliquid mixture. The time spent blending may vary depending on the type of blender used, but generally the slurry may be produced in approximately one minute with a sterilized electric blender, which is further explained below with reference to FIG. 5. Blending the stool sample with a buffer may further include a pH adjustment. A "pH adjustment", in this disclosure, is a change to the acidity and/or basicity of the solution, or stool sample, before combining it with the liquid. Since the buffer allows for little change in the pH level, a pH adjustment may be required beforehand to have the stool sample be at a desired pH level for blending. pH may be adjusted after the stool has been blended with the liquid; at this point the composition may be acidic and so the pH may be titrated up to a pH of 9 using sodium hydroxide that is either 0.5 molar or 1 molar. Moreover, blending the stool sample with a buffer may also involve the use of a comminution device. A "comminution device" is an apparatus that reduces solid materials from one average particle size to a smaller particle size. Comminution device breaks particles of the sample and buffer down so blending of stool sample and the buffer is facilitated. Comminution device may be selected from a group consisting of a crushing device that crushes the solutions before combining them, a grinding device that grinds the sample and buffer before combining them, and a homogenization device that blends the solutions into a homogenous mixture. Comminution device may be any kind of apparatus capable of breaking up, crushing, grinding, cutting, or vibrating particles, such as a mill, crusher, hammer, mallet, or the like.

In some embodiments, the resulting fecal-derived composition may then undergo a form of filtration to separate the large fiber particles from the bacterial and other small molecule components of the stool material. In some embodiments it may then be further concentrated into a microbial pellet. Filtration methods may include centrifugation, vacuum filtration, sieve filtration using gravity, or other mechanistic filtration methods as further explained below. A prepared fecal-derived composition may undergo at least two centrifuge cycles, a first cycle may be used to remove fibrous particulate from the stool-diluent slurry after blending the stool with a buffer. Although any number of centrifuges may be suitable for this step, an example of appropriate equipment may be a Thermo-Fisher Sorvall ST 40 centrifuge suitable for use with 50-milliliter conical tubes. If using such a centrifuge or similar, the slurry may be poured into several 50-milliliter centrifuge conical tubes. In some embodiments, the slurry may be centrifuged for approximately fifteen minutes at approximately 2000 rotation per minute (RPM) or any other suitable RPM. The primary purpose of the first centrifuge cycle is to separate a first fiber pellet from the supernatant, so the time and RPM may vary. The first fiber pellet may be properly and sanitarily discarded, so that the remaining supernatant may be used in the second centrifuge cycle or for processing into the final product.

Still referring to FIG. 13, at step 1320, method 1300 includes stabilizing the fecal-derived composition by lyophilization. In this disclosure, "stabilize" refers to the ability to resist attachment by chemical action; the solution is in equilibrium. Stabilization may be performed by a method called lyophilization. "Lyophilization" is a process of freeze drying wherein the composition is frozen, lowering the pressure, then the ice is removed by sublimation. Sublimation may be used to make food items more stable, more dissolvable in water, or is used as a late-stage purification procedure, like herein. In other words, lyophilization uses freezing to dehydrate the fecal-derived postbiotic composition. Lyophilization may be beneficial since the process maintains nutrients in the compositing as well as giving the composition a longer shelf life. The method also may optionally adjust the pH of the fecal-derived postbiotic composition is adjusted to about 6.0 to about 9.0 prior to lyophilization. For example, but without limitation, a blended, pH-adjusted, sterilized stool batch may be poured into stainless steel sheet trays, wherein each tray may contain approximately 1 liter of stool slurry. These trays may then be placed into a Millrock Stellar Laboratory Freeze Dryer machine, which runs a freeze-drying cycle for approximately 48 hours. Each tray may have a moisture probe that monitors moisture content throughout the run, ensuring that the batch is dried evenly. The freeze-dried powder may then be removed from the freeze-dryer. Samples from each tray could be removed or measured again for moisture content. Moisture content of less than 8% may be considered acceptable. If a batch finishes above 8%, it may be discarded. The powder from all five trays may then be combined, mixed briefly in the commercial food blender, and then sieved for rough filtration of gross particulates to create a single batch. The final powder may be light brown with a fluffy texture and a characteristic earthy odor. To account for interindividual differences in composition, three separate batches from three donors may be combined and assigned a masterbatch ID (e.g., MB001). The powder may then be stored at 4 degrees Celsius until it is encapsulated.

Still referring to FIG. 13, method 1300 may further include removing fiber and particulate matter from the fecal-derived sterilized composition to produce a fecal-derived sterilized prebiotic and postbiotic. "Fibers" in this disclosure are dietary materials containing substances, such as cellulose, that are resistant to the action of digestive enzymes while "particulate matter" is other particles that may limit proper mixing of dried material. Removing fiber and particulate matter from the fecal-derived sterilized composition may then make composition 100 edible and usable. Removing fiber and particulate matter from the fecal-derived sterilized composition may include a combination of removal methods. Combination of removal methods may include filtration. In this disclosure, "filtration" is physical separation process that separates solid matter and fluid from a mixture using a filter medium that has a complex structure through which only the fluid can pass. For example, to separate coffee liquid from the coffee grounds, the mixture is poured over a coffee filter. Other methods of separation that may be used to separate fibers and particulate matter from include, without limitation, centrifugation, sieve filtration, membrane filter press drying, sublimation, flotation, distillation, freezing, chromatography, crystallization, or a combination thereof. If centrifugation is used to prepare the sterilized fecal-derived postbiotic, then the blended stool sample and buffer may be poured into sterilized vials or tubes suitable for use in a centrifuge and undergo at least one centrifugation cycle. Next, the vials may be removed from the centrifuge so that the fiber and large particulate matter pellets may be discarded. A supernatant from the at least first cycle may be poured into new sterilized containers, wherein a "supernatant" denotes the liquid lying above a solid residue after crystallization, precipitation, centrifugation, or other processes. This removal process may be a single step process or can involve one or more of these methods in sequence.

With continued reference to FIG. 13, in other embodiments, the resulting composition after blending may be filtered using another filtration process that is not centrifugation, but rather physical filtration using filter paper or mesh straining. Further processing steps may include the concentration of the supernatant into a bacterial pellet with the option of additional centrifugation. The bacterial pellet obtained after removal of the initial fiber and large particulate removal may be resuspended, for example, at a 1:1 ratio with the fecal supernatant.

Still referring to FIG. 13, method 1300 may also include encapsulating the fecal-derived sterilized prebiotic and postbiotic. Herein, "encapsulate" means to enclose something as if in a capsule or the like. Composition 100 may be encapsulated a plurality of ways depending on if the composition is in a solid or liquid form. Composition 100 may be encapsulated in a solid, an aerosol, a pill, a capsule, a tablet, a paste, a powder, a gel, a lotion, a liquid, an injectable, a parental, a buccal, a sublingual, a nasal, a suppository, or a body wash. Encapsulated formulations can be stored at approximately 20, 5, −20 to −80 degrees Celsius. Some examples of encapsulation methods may include, without limitation, spray drying, spray cooling, extrusion, coacervation, lyophilization and emulsification. It may also be formulated into a food or food product, nutraceutical, supplement, dietary supplement, or other form for oral ingestion. The liquid or lyophilized FSP may be added to a beverage, including a sports beverage. It can be formulated for vaginal or rectal implantation or for administration to a sinus passage via spray or gel. Additional stabilizers may be added to the composition. A stabilizing filler may be added to the oral powder or encapsulated form, such as, but not limited to collagen, glutamine, fiber (e.g., inulin, slippery elm, *psyllium*, chia, flax), or carminatives (e.g., ginger, fennel, rose, licorice, peony). A stabilizing filler may also provide additional benefits to a recipient as a prebiotic, but additional benefits are not necessary as a sterilized fecal composition may be the more important factor in effective treatment of the patient. Effective dose size of composition 100 may vary from as small as about 0.25-0.50 milliliters to about 7.5-15 milliliters of a sterilized un-lyophilized frozen liquid fecal-derived composition. Effective dose sizes for lyophilized powder fecal-derived sterilized composition may vary from as small as about 10 milligrams to about 5 grams.

Figure 14:
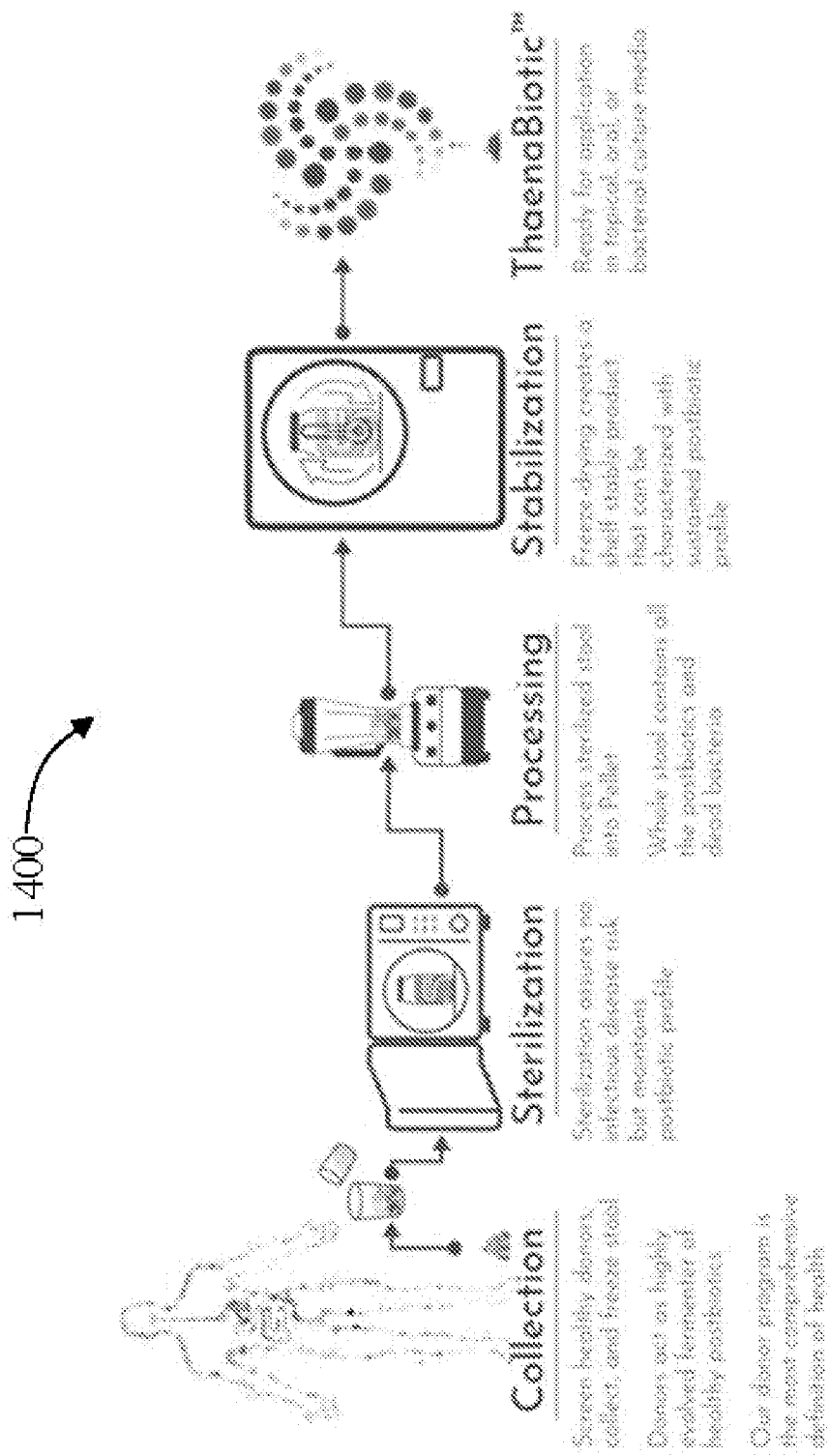
FIG. 14 is a flow diagram representing an outline of an exemplary manufacturing method for a composition.

Now referring to FIG. 14, an outline of an exemplary manufacturing method for the composition is represented through the flow diagram. In brief, the stool sample is collected from healthy donors who match a desired donor profile. Potential donors then may undergo a rigorous screening process to ensure safety and product quality. Once a donor is cleared, stool samples may then be collected, frozen, and stored at negative 20 degrees Celsius until manufacturing begins. Once ready for processing, selected stool samples may be thawed overnight at 4 degrees Celsius. The next day, thawed stools may then be resuspended in distilled water at a 1:1.5 ratio by weight of the stool sample to buffer in autoclavable glass containers. The stools may then be autoclaved at 121 degrees Celsius for 30 min. Individual sterilized stools may then be blended to form a batch. Each batch is then corrected to a pH of 9. The batch may then be lyophilized into a fine, brown powder. Batches are then maybe sifted or filtered to remove any large particulates. Three batches are combined into a single masterbatch, representing the final product. Batches may be combined from the same or different donors.

In some embodiments, the methods described herein may also include the placing of the stool sample from the healthy, screened donor in an autoclaved container suitable for blending. In some embodiments, an autoclaved buffer solution or water may be added to the container, depending on the condition of the donor stool. The stool and buffer solution may be blended together to produce a fecal slurry. This method may include adding a buffered solution of PBS, maldextrin-trehalose solution, or deionized water (DI H20) before, during, and/or after the homogenization. The homogenized slurry can be produced in a blender or using another suitable homogenization method, including but not limited to mashing in a bag. The method may next include the step of filtering bulk fiber and large particulate matter from the homogenized mixture. Separation of the large particulate and fiber may occur through physical filtration using filter paper or mesh straining. Alternatively, centrifugation can be used for filtration. These stages may include the following, without limitation: recruiting potential donors, rigorous screening of potential donors, selecting qualified donors, providing stool donor instructions, transporting stool samples, receiving said samples in a laboratory, producing capsules or product, tracking, delivery, and outcome reporting.

Composition 100 may be consistently manufactured to meet the established specifications and does not contain unacceptable levels of contaminants. Analytical methods were used to confirm the product's composition, sterility, and safety. In addition, toxicological modeling revealed that composition 100 may be more protective than vitamin C, the positive control, in a reactive oxygen species assay using *C. elegans*. In this disclosure, "*C. elegans*" is as a model organism to study human diseases ranging from Parkinson's disease to mitochondrial diseases, as well as studying the immune system. Composition 100 demonstrated protection against oxidative stress in *C. elegans* in a dose dependent manner. Additionally, and at lower concentrations in the Zebrafish model, there was a significant increase in larval photo motor response observed. Anecdotal clinical data from use on well over a hundred patients has also provided promising results, demonstrating a safe and tolerable product.

What is claimed is:

1. A method for manufacturing a composition for a fecal-derived sterilized prebiotic and postbiotic, the method comprising:

collecting a pre-donation stool sample from a donor, wherein collecting the pre-donation stool sample from the donor further comprises:

collecting a serum sample from the donor;

testing the pre-donation stool sample for presence of infectious disease symptoms, wherein testing the pre-donation stool sample is done within 14 days of collection of the pre-donation stool sample;

testing the serum sample in response to qualifying the pre-donation stool sample by testing the pre-donation stool sample; and determining that the donor is healthy based on the testing of the pre-donation stool sample and the serum sample;

collecting a donation stool sample from the donor, wherein the donation stool sample is frozen;

sterilizing the donation stool sample while retaining a bacterial plurality of biological macromolecules;

blending the donation stool sample with a liquid to create a fecal-derived composition;

identifying a PH of the fecal-derived composition;

increasing the PH of the fecal-derived composition to value of at least 7.2 prior to lyophilization to maintain a plurality of short chain fatty acids during the lyophilization;

stabilizing the fecal-derived composition by the lyophilization, wherein the lyophilization results in a freeze-dried, sterilized fecal-derived composition with fiber and particulate matter included;

monitoring, by a moisture probe, a moisture content of the freeze-dried, sterilized fecal-derived composition;

confirming that the moisture content of the freeze-dried, sterilized fecal-derived composition is less than 8%; and verifying that the composition includes a respective ratio by weight of acetic acid:propionic acid:butyric acid of 60±10:20±10:20±10.

2. The method of claim 1, further including removing fiber and particulate matter from the fecal-derived sterile composition to produce a fecal-derived sterile prebiotic and postbiotic.

3. The method of claim 1, further including encapsulating the fecal-derived sterile prebiotic and postbiotic.

4. The method of claim 1, wherein the liquid used to blend the donation stool sample is a buffer.

5. The method of claim 1, wherein the liquid used to blend the donation stool sample is water.

6. The method of claim 1, wherein sterilizing the donation stool sample includes autoclaving.

7. The method of claim 1, wherein blending the donation stool sample comprises utilizing a comminution device.

8. The method of claim 1, wherein increasing the PH of the fecal-derived composition to value of at least 7.2 prior to lyophilization to maintain a plurality of short chain fatty acids during the lyophilization comprises increasing the PH of the fecal-derived composition using sodium hydroxide.

* * * * *